(12) United States Patent
Kageyama et al.

(10) Patent No.: US 8,216,799 B2
(45) Date of Patent: Jul. 10, 2012

(54) DRY ANALYTICAL ELEMENT FOR LIPASE MEASUREMENT

(75) Inventors: Shigeki Kageyama, Tokyo (JP); Hideaki Tanaka, Asaka (JP)

(73) Assignee: Fujifilm Corporation, Tokyo (JP)

( * ) Notice: Subject to any disclaimer, the term of this patent is extended or adjusted under 35 U.S.C. 154(b) by 1000 days.

(21) Appl. No.: 12/155,890

(22) Filed: Jun. 11, 2008

(65) Prior Publication Data
US 2009/0011450 A1 Jan. 8, 2009

(30) Foreign Application Priority Data
Jun. 12, 2007 (JP) ................. 2007-155194

(51) Int. Cl.
*C12Q 1/44* (2006.01)
*C12Q 1/34* (2006.01)
(52) U.S. Cl. .......................... 435/19; 435/18
(58) Field of Classification Search .............. 435/18, 435/19
See application file for complete search history.

(56) References Cited

U.S. PATENT DOCUMENTS
4,555,483 A 11/1985 LiMuti et al.

FOREIGN PATENT DOCUMENTS

| EP | 0 101 046 A1 | 2/1984 |
|---|---|---|
| JP | 59-48098 A | 3/1984 |
| JP | 4-316500 A | 11/1992 |
| JP | 9-154598 A | 6/1997 |
| JP | 2002-125699 A | 5/2002 |
| WO | WO-01/01960 A1 | 1/2001 |
| WO | WO-2006/060652 A2 | 6/2006 |

OTHER PUBLICATIONS

Tetrault G., "Lipase Activity in Serum Measured with Ektachem is Often Increased in Nonpancreatic Disorders", Clin. Chem., vol. 37, No. 3, pp. 447-451, 1991.

*Primary Examiner* — Herbert J Lilling
(74) *Attorney, Agent, or Firm* — Birch, Stewart, Kolasch & Birch, LLP

(57) ABSTRACT

It is an object of the present invention to provide a dry analytical element for pancreatic lipase analysis having high selectivity with respect to pancreatic lipase, whose multianalyte correlation has been improved. The present invention provides a dry analytical element for measurement of pancreatic lipase contained in a body fluid, which comprises at least one development layer and/or reagent layer containing diglyceride or triglyceride of long-chain alkyl fatty acid having 12 to 22 carbon atoms, monoglyceride lipase, and a glycerine measurement reagent, wherein the development layer and/or the reagent layer comprise two or more types of anionic surfactants and at least one type of the anionic surfactant is alkylarylsulfonate.

17 Claims, 3 Drawing Sheets

DRY ANALYTICAL ELEMENT FOR LIPASE MEASUREMENT

TECHNICAL FIELD

The present invention relates to a method for producing a dry analytical element for measurement of lipase activity (particularly pancreatic lipase activity) in a liquid sample such as, in particular, serum and plasma of humans or animals, such analytical element being available for convenient use and having good accuracy. The dry analytical element produced in the present invention is particularly useful for diagnosing human and canine pancreatic diseases.

BACKGROUND ART

Pancreatic lipase analysis, which is useful for pancreatic disease diagnosis, is often carried out by measuring pancreatic lipase under conditions in which a micellar substrate is dispersed in water in view of the fact that pancreatic lipase functions in oil-water interface. This is because non-pancreatic lipase such as lipoprotein lipase, liver lipase, or esterase reacts with a substrate solubilized with a surfactant or the like or with glyceride of fatty acid having short alkyl chains. Thus, it is considered that a technically important point for development of dry analytical elements for pancreatic lipase is the incorporation of glyceride of a long-fatty-acid (serving as a substrate), which is specific to pancreatic lipase, into such analytical element, in a state that the glyceride is specific to pancreatic lipase.

Dry analytical elements used for lipase analysis are roughly classified into two groups. An example of a first group is a multilayer dry analytical element (JP Patent Publication (Kokai) No. 59-48098 A (1984)) according to a method wherein triglyceride is used as a substrate and is converted into a dye via glycerine and hydrogen peroxide. According to the first disclosed method, a triglyceride having a long-chain alkyl group having at least 8 carbon atoms at an ester position (α position) and having a short-chain alkyl group at two other esters each is used as a substrate, 1,2 diacetylglyceride generated by lipase in a specimen is converted into glycerine with the use of an esterase (namely, acetinase), and glycerine is converted into a dye. The above method is a convenient and highly accurate lipase measurement method. However, it has been reported that selectivity with respect to pancreatic lipase is not high, and thus the method is problematic for diagnosis of pancreatic diseases (Clin. Chem., 37/3, 447-451 (1991)).

Next, a method using a dry chemistry reagent for pancreatic lipase analysis, such reagent comprising triglyceride (serving as a substrate) comprising a long chain fatty acid (e.g., triolein) having 14 to 20 carbon atoms, monoglyceride lipase, and a glycerine measurement reagent is disclosed in JP Patent Publication (Kokai) No. 4-316500 A (1992). Further, a method wherein a highly accurate multilayer analytical element is prepared according to the above method and fine particles are further incorporated into the element in order to improve lipase reactivity is disclosed in JP Patent Publication (Kokai) No. 2002-125699 A. In the method of JP Patent Publication (Kokai) No. 4-316500 A (1992), highly fat-soluble substrate is incorporated, so that a protective colloid such as gum Arabic is used for aqueous system dispersion using ultrasonic dispersion (JP Patent Publication (Kokai) No. 4-316500 A (1992): Examples). Accordingly, it is necessary to maintain the reproducibility of substrate dispersion and uniformity in particle size distribution, and it is thought that production of such element is difficult.

For instance, JP Patent Publication (Kokai) No. 4-316500 A (1992) contains the following description: "triglyceride, such as triolein, comprising a long chain fatty acid in each of three ester positions has the property of being emulsified with difficulty. Thus, even if a solution in which triolein has been uniformly emulsified and dispersed via agitation or by physical shearing force generated by ultrasound waves or the like is added in the presence of a surfactant or a protective colloid upon preparation of a dry reagent, water serving as a dispersion medium disappears when the reagent becomes dry, and thus an emulsified product aggregates or coalesces so as to adhere to the surface of a development layer, resulting in significant reduction in the surface area in oil-water interface. Upon measurement, even if a specimen (liquid) containing lipase is allowed to react with such dry reagent, triolein remains in a state of aggregating or coalescing and thus does not return to the original state of being dispersed because of lack of physical shearing force. The reaction field of lipase is an oil-water interface. Thus, a decrease in the surface area of an oil-water interface is thought to cause a decrease in reaction rate."

An example of a second group is a dry analytical element obtained by a method using 1,2-O-dilauryl-rac-glycero-3-glutaric acid/resorufin ester serving as a dye-releasing substrate (JP Patent Publication (Kokai) No. 9-154598 A (1997)). Such method is a preferable because high specificity with respect to pancreatic lipase can be achieved and a glycerine coloring system is unnecessary. However, the substrate incorporated into a dry analytical element is highly likely to degrade. Thus, such dry analytical element has still not been available in practice, although it has been attempted to separate a low-pH layer containing a lipase substrate from another high-pH reagent layer. In addition, in such case, an ether system solvent that is thought to be preferable for dissolution of a substrate imposes significant environmental burdens and thus is seriously problematic in terms of production suitability in the present situation in which environmentally-friendly designs are strongly required. Further, the relatively high price of such a substrate is also problematic in terms of practical use.

As described above, the product disclosed in JP Patent Publication (Kokai) No. 59-48098 A (1984) is still the only commercially available dry analytical element for lipase analysis, although the product has low pancreatic lipase specificity. Thus, dry analytical elements that are excellent in terms of reliability for diagnosis of pancreatic diseases have been desired in the market.

DISCLOSURE OF THE INVENTION

It is an object of the present invention to provide a dry analytical element for pancreatic lipase analysis having high selectivity with respect to pancreatic lipase, whose multianalyte correlation has been improved.

As a result of intensive studies directed towards achieving the aforementioned object, the present inventors have found that a dry analytical element for pancreatic lipase analysis with an improved multianalyte correlation can be provided by containing two or more types of anionic surfactants in a dry analytical element comprising long-chain fatty acid glyceride (preferably triglyceride) used as a substrate, monoglyceride lipase, and a glycerine measurement reagent, thereby completing the present invention.

The present invention provides a dry analytical element for measurement of pancreatic lipase contained in a body fluid, which comprises at least one development layer and/or reagent layer containing diglyceride or triglyceride of long-chain alkyl fatty acid having 12 to 22 carbon atoms, monoglyceride lipase, and a glycerine measurement reagent, wherein the development layer and/or the reagent layer comprise two or more types of anionic surfactants and at least one type of the anionic surfactant is alkylarylsulfonate.

Preferably, the alkylarylsulfonate is alkylbenzenesulfonate.

Preferably, the alkylbenzenesulfonate is alkylbenzenesulfonate, the chain length of an alkyl group of which consists of 10 to 14 carbon atoms.

Preferably, the alkylbenzenesulfonate is a linear dodecylbenzenesulfonic acid sodium salt.

Preferably, the amount of alkylarylsulfonate added is 0.1 to 10 g/m$^2$.

Preferably, the triglyceride is triolein.

Preferably, the monoglyceride lipase is a monoglyceride lipase which does not act on diglyceride and triglyceride substantially. More preferably, the monoglyceride lipase is *Bacillus stearothermophilus* H-165-derived monoglyceride lipase.

Preferably, the glycerine measurement reagent is composed of glycerol kinase, glycerophosphate oxidase, and a coloring reagent.

Preferably, the dry analytical element is composed of a water-impermeable support, a reagent layer, and a development layer.

Preferably, the development layer is made of fabric or a porous membrane.

Preferably, the porous membrane is a porous membrane formed with polyvinylsulfone or acetylcellulose or a porous membrane formed with microbeads.

Preferably, the amount of monoglyceride lipase added is 8000 U/m$^2$ to 1000 U/m$^2$.

Preferably, the dry analytical element of the present invention is produced by a method comprising a step of adding diglyceride or triglyceride dissolved in lower alcohol or acetone to a development layer or a reagent layer and then drying it.

Preferably, the method of drying diglyceride or triglyceride is hot-air drying.

Preferably, diglyceride or triglyceride is dissolved in methanol, ethanol, propyl alcohol, or acetone.

Another aspect of the present invention provides a method for measuring pancreatic lipase contained in a body fluid, which comprises applying a body fluid to the dry analytical element of the present invention as mentioned above.

Preferably, the body fluid is canine blood.

By producing a dry analytical element for measurement of pancreatic lipase using triolein as a substrate, it became possible to carry out pancreatic lipase-specific analysis. However, the correlation coefficient of the multianalyte correlation has not been improved. The cause was analyzed. As a result, it was found that activation of pancreatic lipase due to colipase was insufficient depending on the type of an analyte. In the present invention, it has been found that pancreatic lipase as an analyte can be activated without increasing the amount of expensive colipase by adding anionic surfactants such as linear sodium dodecylbenzenesulfonate. As a result, the correlation coefficient of the multianalyte correlation was greatly improved in an analysis using the dry analytical element for measurement of pancreatic lipase of the present invention.

BEST MODE FOR CARRYING OUT THE INVENTION

Figure 1:
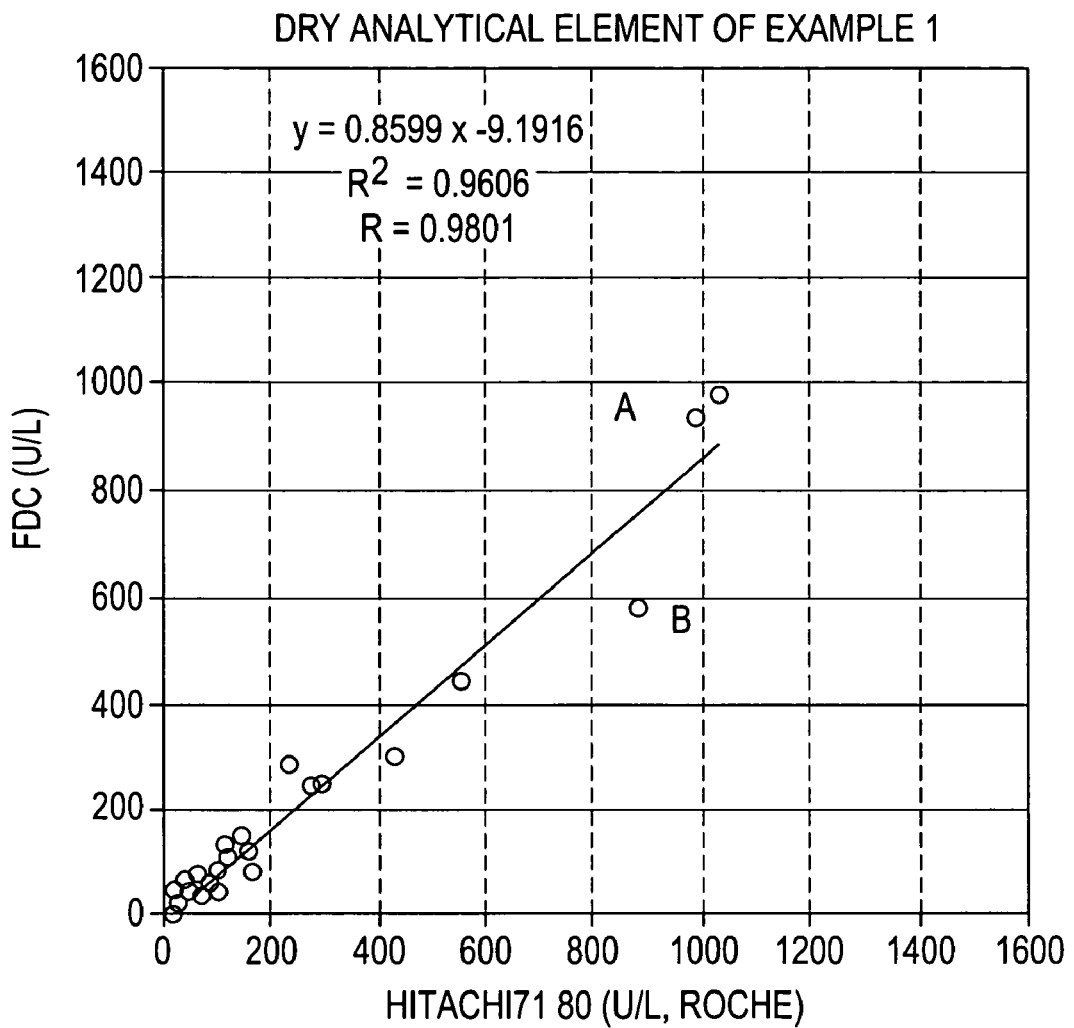
FIG. 1 shows the results of an analysis using the dry analytical element of Example 1.

The dry analytical element for measurement of pancreatic lipase contained in a body fluid of the present invention is a dry analytical element used for the measurement of pancreatic lipase contained in a body fluid, which comprises at least one development layer and/or reagent layer containing diglyceride or triglyceride of long-chain alkyl fatty acid having 12 to 22 carbon atoms, monoglyceride lipase, and a glycerine measurement reagent, and which is characterized in that the aforementioned development layer and/or reagent layer comprise two or more types of anionic surfactants and at least one type of the anionic surfactant is alkylarylsulfonate.

In an analysis using a dry analytical element, since an analyte is subjected to the analysis without dilution, various components contained in the analyte have an influence upon the analysis. The present inventors have found for the first time that a difference in lipase activation among analytes, which had not been problematic in analytical methods using a diluted analyte, occurs in analyses using a dry analytical element. In the present invention, the inventors have found that in order to solve such a problem regarding a difference in lipase activation among analytes, addition of alkylphenylsulfonate such as sodium dodecylbenzenesulfonate is useful. That is to say, in the analyses using the conventional dry analytical element, a multianalyte correlation has been poor due to poor lipase reactions caused by some analytes. In order to solve such a problem, alkylphenylsulfonate such as sodium dodecylbenzenesulfonate was added to a dry analytical element in the present invention, so that the inventors succeeded in significantly improving a correlation coefficient. This effect was obtained as a result of the recovery of the lipase activity of an analyte that had a negative error in a correlation.

The dry analytical element of the present invention comprises two or more types of anionic surfactants, and at least one of them is alkylarylsulfonate.

Examples of an anionic surfactant used in the present invention include surfactants having a carboxyl group, a sulfonic acid group, a sulfate group or a phosphate as a hydrophilic group. Preferred anionic surfactants having a sulfonic acid group that can be used in the present invention include alkylbenzenesulfonate, alkylnaphthalenesulfonate, alkylsulfate, a polyoxyethylene alkyl ether sulfate, α-olefin sulfonate, and N-acylmethyl taurine salts. It is preferable that a hydrophobic group have approximately 12 to 20 carbon atoms. Of these, anionic surfactants that do not inhibit lipase activity and do not deactivate enzyme added to the dry analytical element, are preferable.

Of these, alkylbenzenesulfonate is preferable, and alkylbenzenesulfonate having an alkyl chain containing 10 to 14 carbon atoms is more preferable. Linear dodecylbenzenesulfonate containing 12 carbon atoms, which is a main component of detergent, is further more preferable. As a salt, a sodium salt is preferable. However, a potassium salt or a lithium salt can also be used. After addition of alkylbenzenesulfonate, salts may be formed in the dry analytical element.

As an anionic surfactant having a carboxy group, a bile salt having lipase-activating action is preferable. Preferred examples of such a bile salt include deoxycholate, cholate, taurocholate, taurodeoxycholate, and deoxytaurocholate. Sodium deoxycholate and sodium taurodeoxycholate are particularly preferable.

The optimal combination of anionic surfactants in the present invention is sodium deoxycholate or sodium taurodeoxycholate and linear dodecylbenzenesulfonate.

The amount of alkylarylsulfonate added in the present invention is not particularly limited, as long as the effects of the invention can be achieved. The amount of alkylarylsulfonate added is preferably 0.1 to 10 g/m$^2$, more preferably 0.2 to 5 g/m$^2$, and further more preferably 0.5 to 5 g/m$^2$.

Glyceride used in the present invention is diglyceride or triglyceride of long-chain alkyl chain fatty acid. Such a long-chain alkyl chain may be either saturated or unsaturated. From the viewpoint of selectivity with respect to pancreatic lipase, the alkyl chain length of such long-chain alkyl chain fatty acid may be 12 to 22 carbon atoms, and preferably 16 to 20 carbon atoms. Examples of such fatty acid are given below. Examples of saturated fatty acid include lauric acid ($C_{12:0}$), myristic acid ($C_{14:0}$), palmitic acid ($C_{16:0}$), stearic acid ($C_{18:0}$), arachidic acid ($C_{20:0}$), and behenic acid ($C_{22:0}$). Examples of unsaturated fatty acid include palmitoleic acid ($C_{16:1}$), petroselinic acid ($C_{11}H_{23}COOH$), oleic acid ($C_{18:1}$), linolic acid ($C_{18:1}$), linolenic acid ($C_{18:2}$), elestearic acid ($C_{18:3}$), and arachidonic acid ($C_{20:4}$). Preferred examples of such glyceride include the glycerides of oleic acid and linolic acid. A particularly preferred glyceride is triolein, which is a triglyceride of oleic acid.

Moreover, in the present invention, monoglyceride lipase that does not substantially react with diglyceride, and a conventionally existing highly reliable glycerine coloring reagent are used. As a layer structure, at least one development layer or reagent layer may be adopted, and a single layered test paper may also be used. In order to enhance measurement precision and intensity, a multilayer analytical element consisting of a support and at least one reagent layer is preferably used. As to the substrate, glyceride such as triolein can be dissolved in an organic solvent such as ethanol, and the solution is incorporated into a dry analytical element, and then preferably dried by hot-air drying.

A light-permeable and/or water-impermeable support can be used to constitute a support layer of the dry analytical element for lipase measurement of the present invention. Examples of a light-permeable/water-impermeable support include a film- or sheet-type transparent support having a thickness of approximately 50 μm to 1 mm and preferably approximately 80 μm to 300 μm and comprising polymers such as polyethylene terephthalate, polycarbonate of bisphenol A, polystyrene, cellulose ester (e.g., cellulose diacetate, cellulose triacetate, or cellulose acetate propionate), or the like.

An undercoat layer is provided on the surface of a support according to need such that adhesion between a reagent layer provided on the support and the support can be strengthened. In addition, physical or chemical activation treatment is carried out on the support surface, instead of provision of an undercoat layer, such that adhesivity can be improved.

A reaction (reagent) layer is provided on a support (via another layer such as an undercoat layer in some cases). A reaction (reagent) layer is a water-absorbing and water-permeable layer containing a hydrophilic polymer binder in which at least a portion of a reagent composition described below, such composition reacting with lipase serving as an analyte so as to cause optically detectable changes, is substantially uniformly dispersed.

A hydrophilic polymer that can be used as a binder for a reagent layer is generally a natural or synthetic hydrophilic polymer having a swelling rate at 30° C. in the range of approximately 150% to 2000% and preferably of approximately 250% to 1500%. Examples of such hydrophilic polymer include gelatins (e.g., acid-treated gelatin and deionized gelatin), gelatin derivatives (e.g., phthalated gelatin and hydroxyacrylate graft gelatin), agarose, pullulan, pullulan derivatives, polyacrylamide, polyvinyl alcohol, and polyvinylpyrrolidone, which are disclosed in JP Patent Publication (Kokai) No. 58-171864 A (1983), JP Patent Publication (Kokai) No. 60-108753 A (1985), and the like.

A reaction (reagent) layer may be a layer that has been appropriately cross-linked and insolubilized using a crosslinking reagent. Examples of a crosslinking reagent include: conventional vinyl sulfone crosslinking reagents (such as 1,2-bis(vinyl sulfonylacetamide) ethane and bis(vinyl sulfonylmethyl)ether) and aldehyde and the like, for gelatin; and aldehyde and epoxy compounds comprising two glycidyl groups and the like, for methallyl alcohol copolymer.

The thickness of a reaction (reagent) layer when dried is preferably in the range of approximately 1 μm to 100 μm and more preferably of approximately 3 μm to 30 μm. Preferably, a reagent layer is substantially transparent.

According to the present invention, it is preferable to use a fabric development layer as a development layer. Alternatively, it is also possible to use a non-fabric material such as a porous membrane comprising polyvinylsulfone or acetylcellulose, porous membrane formed with microbeads, glass fiber filter paper, or filter paper.

Examples of such porous development layer made of fabric include woven fabric development layers (e.g., plain weave fabric such as broadcloth or poplin) described in JP Patent Publication (Kokai) No. 55-164356 A (1980), JP Patent Publication (Kokai) No. 57-66359 A (1982), and the like; knitted fabric development layers (e.g., tricot knitted fabric, double tricot knitted fabric, and Milanese knitted fabric) described in JP Patent Publication (Kokai) No. 60-222769 A (1985) and the like; and a development layer comprising woven fabric or knitted fabric subjected to etching treatment with an alkaline etching solution described in JP Patent Publication (Kokai) No. 1-172753 A (1989). Knitted fabric is preferable. In particular, tricot knitted fabric is preferable. Examples of fabric material used include polyester, cotton, nylon, silk, vinylon, rayon, polyamide, acrylic, wool, polypropylene, and hemp. Preferably, polyester is used. The appropriate thickness of a development layer is approximately 50 to 400 μm and preferably approximately 200 to 300 μm. The porosity of fabric is approximately 20% to 90% and preferably approximately 40% to 85%.

In the cases of woven fabric and knitted fabric used for a porous development layer, it is possible to improve the adhesivity of such fabric to a lower layer (close to a support) by carrying out a physical activation treatment represented by a glow discharge treatment or corona discharge treatment disclosed in JP Patent Publication (Kokai) No. 57-66359 A (1982) on at least one-side of the fabric or by hydrophilizing the fabric in a manner such that a washing and degreasing treatment and/or a hydrophilization treatment involving surfactant dipping, hydrophilic polymer dipping, or the like, which are disclosed in JP Patent Publication (Kokai) No. 55-164356 A (1980), JP Patent Publication (Kokai) No. 57-66359 A (1982) and the like, are carried out, or such that a treatment involving an appropriate combination of the above treatments is carried out in a sequential manner.

When a porous layer is used as a development reaction layer, a porous medium thereof may be fibrous or nonfibrous. Examples of a fibrous material that can be used include filter paper, nonwoven fabric, woven fabric (e.g., plain weave fabric), knitted fabric (e.g., tricot knitted fabric), and glass fiber filter paper. Examples of a nonfibrous material include a membrane filter comprising cellulose acetate and the like disclosed in JP Patent Publication (Kokai) No. 49-53888 A (1974), and a particulate unit layer having continuous voids, such layer comprising fine particles of an inorganic or organic substance disclosed in JP Patent Publication (Kokai) No. 49-53888 A (1974), JP Patent Publication (Kokai) No. 55-90859 A (1980) (corresponding to U.S. Pat. No. 4,258,001), JP Patent Publication (Kokai) No. 58-70163 A (1983) (corresponding to U.S. Pat. No. 4,486,537), and the like. Also, layer laminated products having a plurality of porous layers that partially adhere to each other disclosed in the following documents and the like are preferable: JP Patent Publication (Kokai) No. 614959 A (1986) (corresponding to EP 0166365 A); JP Patent Publication (Kokai) No. 62-116258 A (1987); JP Patent Publication (Kokai) No. 62-138756 A (1987) (corresponding to EP 0226465 A); JP Patent Publication (Kokai) No. 62-138757 A (1987) (corresponding to EP 0226465 A); and JP Patent Publication (Kokai) No. 62-138758 A (1987) (corresponding to EP 0226465 A).

In order to add reagents to a development layer, a development layer is first formed and then reaction reagents may be added by means of coating or the like. Alternatively, an example of a useful method is the method described in JP Patent Publication (Kokai) No. 55-164356 A (1980), comprising of dipping or coating to a porous membrane composed of paper, fabric or the like with the reagents of the present invention and allowing the resultant to adhere to another water-permeable layer formed on a support.

A porous layer may be a development layer having a so-called measuring function that allows a supplied liquid to be developed in an area that is almost in proportion to the amount of the liquid. It is effective to control such function with the use of surfactants and hydrophilic binders.

It is also possible to provide a layer that differs from the above layers to the dry analytical element of the present invention. Examples thereof include a light-shielding layer, a water-absorbing layer, and an adhesive layer.

In the measurement reaction system used in the present invention, diglyceride or triglyceride serving as a substrate is degraded with lipase to be measured, and monoglyceride generated upon such degradation is degraded with monoglyceride lipase. L-α-glycerophosphate is generated from the glycerol with the use of glycerol kinase. Then, L-α-glycerophosphate is turned into dihydroxyacetone phosphate with L-α-glycerophosphate oxidase, and also hydrogen peroxide is generated. Coloring from a coloring dye is induced by the function of peroxidase with the use of hydrogen peroxide.

Monoglyceride lipase is added to a reagent system that is incorporated into the dry analytical element of the present invention. A preferred example of monoglyceride lipase is one that does not substantially react with triglyceride and diglyceride but reacts with monoglyceride of long chain fatty acid. *Bacillus stearothermophilus* H-165-derived monoglyceride lipase described in JP Patent Publication (Kokai) No. 63-245672 A (1988) and JP Patent Publication (Kokai) No. 4-316500 A (1992) is particularly preferable.

Glycerol kinase allows glycerol and ATP to react with each other so as to change them into L-α-glycerophosphate (L-glycerol-3-phosphate) and ADP, respectively. It uses $Mg^{2+}$ and $Mn^{2+}$ as coenzymes.

L-α-glycerophosphate oxidase (glycerol-3-phosphate oxidase) oxidizes L-glycerophosphate so as to change it into dihydroxyacetone phosphate and generate hydrogen peroxide.

Various coloring systems in which coloring is caused by the function of peroxidase with the use of hydrogen peroxide have been developed for dry analytical elements. Thus, it is possible to appropriately select and use one thereof. Most of them are leuco dyes, and typical examples thereof include o-toluidine.

In order to increase reactivity of pancreatic lipase (mainly contained in blood) that serves as a substance to be measured of the present invention, it is preferable to add colipase to a reagent system incorporated into the dry analytical element of the present invention. A preferred example of colipase is pig-pancreas-derived colipase. In addition, in order to increase the activity of pancreatic lipase and to reduce the lipase activity of non-pancreatic lipase, deoxycholic acid or taurocholic acid may be added as an activating reagent. Thus, influences of esterase, liver lipase, and lipoprotein lipase are removed, and thus pancreatic lipase can be measured with high specificity.

The contents of the above reagents are as follows:
triglyceride: approximately 0.1 to 15 $g/m^2$ and preferably approximately 0.5 to 10 $g/m^2$;
glycerol kinase: 0.5 to 100 $KU/m^2$ and preferably approximately 1 to 10 $KU/m^2$;
L-α-glycerophosphate oxidase: approximately 2 to 200 $KU/m^2$ and preferably approximately 5 to 50 $KU/m^2$;
peroxidase: approximately 1 to 200 $KU/m^2$ and preferably approximately 5 to 50 $KU/m^2$;
monoglyceride lipase: approximately 2 to 100 $KU/m^2$ and preferably approximately 3 to 30 $KU/m^2$;
coloring dye: approximately 0.05 to 2.00 $g/m^2$ and preferably approximately 0.1 to 1.00 $g/m^2$;
colipase: preferably 0.010 to 0.400 $g/m^2$ (5 to 200 $KU/m^2$); and
deoxycholic acid: approximately 0.1 to 10 $g/m^2$.

Monoglyceride lipase used herein is in an amount of preferably 8000 $U/m^2$ to 1000 $U/m^2$, more preferably 6000 $U/m^2$ to 2000 $U/m^2$, and the most preferably 4300 $U/m^2$ to 2000 $U/m^2$. Although monoglyceride lipase is a conjugated enzyme, it is not preferable to add it in an excessive amount. When diglyceride is used as a substrate, the background level might be increased. In addition, even when triglyceride is used as a substrate, the reaction of a part of lipoprotein in blood is induced along with increases in the amount of monoglyceride lipase, resulting in the generation of measurement errors.

The total amount of such reagent composition may be contained in a reagent layer or development layer. Alternatively, it may be divided such that it is contained in both layers, or it may be partially contained in another layer.

It is also possible to add other reagents, such as a buffer and a surfactant, to the dry analytical element of the present invention.

Examples of a buffer that can be contained in the dry analytical element of the present invention include known buffers such as a carbonate buffer, a borate buffer, a phosphate buffer, a tris salt buffer, and a Good's buffer. These buffers can be selected and used by referring to known references such as "Primary Experimental Methods for Proteins and Enzymes (*Tanpakushitsu/Koso no Kiso Jikken-hou*)" (Takeichi Kajio et al., Nankodo Co., Ltd., 1981). The content thereof may be approximately equal to that generally used in an integrated multilayer analytical element, which is in the range of approximately 100 mg/m² to 5.0 g/m² and preferably of approximately 500 mg/m² to 3.0 g/m².

A development layer or reaction layer of the analytical element of the present invention may contain a surfactant such as a nonionic surfactant, in addition to the aforementioned anionic surfactants. A surfactant used contains a combination of a lipophilic group (e.g., an alkyl group, an alkylphenyl group, a styrenated phenyl group, a benzilphenyl group, or a sorbitanalkyl group), and a hydrophilic group (a polyoxyethylene group, or a polyglycerol group, and a polyoxyethylenepolypropylene polymer). Examples of such surfactant include polyoxyethylene alkylether, polyoxyethylene branched alkylether, polyoxyalkylene alkylether, polyoxyethylene alkylphenylether, and alkylphenyl polyglyceride. Specific examples thereof include polyoxyethylene tridecylether, polyoxyethylene branched decylether, polyoxyethylene p-octylphenyl ether, polyoxyethylene p-octylphenyl ether, polyoxyethylene p-nonylphenyl ether, polyoxyethylene oleyl ether, polyoxyethylene sorbitan monolaurate, p-nonylphenoxypolyglycidol, and octylglucoside. Among such nonionic surfactants, polyoxyethylene tridecylether, polyoxyethylene branched decylether, p-octylphenoxypolyethoxyethanol, p-nonylphenoxypolyethoxyethanol, p-nonylphenoxypolyglycidol, and the like are preferable. A nonionic surfactant is allowed to be contained in a development layer such that a function of developing an aqueous liquid sample (metering function) is further improved. A nonionic surfactant is allowed to be contained in a reaction layer, thereby water contained in an aqueous liquid sample is facilitated to be absorbed to a reaction layer in a substantially uniform manner upon analysis operations. Also in such case, the liquid comes into contact with a development layer in a rapid and substantially uniform manner.

In addition, a development layer may also contain a hydrophilic polymer. Examples of a hydrophilic polymer include starch, cellulose, cellulose derivatives (e.g., methylated cellulose, hydroxyethylated cellulose, and hydroxypropylated cellulose), agarose, gelatins (e.g., an acid-treated gelatin and a deionized gelatin), gelatin derivatives (e.g., a phthalated gelatin and a hydroxyacrylate graft gelatin), acrylamide polymers, copolymers each comprising acrylamide and a various vinyl monomer, vinylpyrrolidone polymers, copolymers each comprising vinylpyrrolidone and a various vinyl monomer, acrylate polymers, and copolymers each comprising acrylate and a various vinyl monomer. Among the above hydrophilic polymers, vinylpyrrolidone derivatives and cellulose derivatives are preferable.

A preferred production method is described below. A binder such as gelatin and a surfactant are added to a support. A water-soluble coating solution having improved film-forming properties is coated thereto and dried, so that a reagent layer is prepared. A development layer is obtained as follows when fabric or a formed porous membrane is used as a development layer. Water is added to a part of a reagent layer such that the part is solubilized. A binder is further softened (by heating according to need) and then it is fixed by applying pressure to a development layer membrane and a reagent layer on the support, followed by drying.

Hitherto, in the case of a method for dispersing triolein in water, which is used as a method for adding triolein to an analysis solution or dry analysis apparatus for lipase, the glyceride particle size is unstable due to changes in terms of the time for the addition of a reagent, the stirring efficiency, the solution temperature, and the like, although the particles are stabilized with a surfactant or a protective colloid. Thus, intra-lot or lot-to-lot variations are significant so that it is difficult to produce a dry analysis apparatus for lipase with good accuracy. Further, it is believed that an expensive and advanced dispersion apparatus is necessary for such dispersion and emulsification. In addition, particle sedimentation occurs unless the size of dispersed particles becomes small. Such sedimentation is problematic for preparation of uniform analysis apparatuses.

According to a method for solubilizing triglyceride or diglyceride in a water-soluble solution containing a surfactant so as to add the solution to a dry analysis apparatus, not only the reactivity of pancreatic lipase but also the reactivity of non-pancreatic lipase or esterase to the substrate thereof may be increased in some cases. In addition, a surfactant might deactivate a conjugated enzyme. Such outcomes are not preferable.

Thus, if necessary in order to dissolve glyceride (lipase substrate) such as triolein in a lower alcohol or acetone so as to improve coating properties, a binder such as polyvinylpyrrolidone is added to control viscosity. Preferably, such lower alcohol or acetone is a lower alcohol solvent having 1 to 6 carbon atoms or acetone. In particular, methanol, ethanol, propyl alcohol, and acetone are preferable. Among them, ethanol is particularly preferable. It is not preferable to use an ether solvent such as tetrahydrofuran or dioxane. One reason for this is that a water soluble polymer (e.g., polyvinylpyrrolidone) that is useful for improved coating properties and improved developing property of body fluid becomes less soluble in a case involving the use of such an ether solvent. Chloroform and methylene chloride are useful because glyceride dissolves well therein. However, in recent years, environmental toxicity such as carcinogenicity has been problematic, so that the use thereof requires attention and is not preferred.

Regarding the ratio of the amount of glyceride to that of the solvent, preferably, 1 g of triolein is used for 50 to 300 g of ethanol when triolein is dissolved in ethanol, for example. More preferably, 1 g of triolein is used for 100 to 200 g of ethanol. When the triolein concentration is high, triolein is not dissolved in ethanol, and thus it becomes difficult to uniformly add triolein. For a method for adding glyceride to a solvent solution, coating or dipping may be carried out. Regarding such method for adding glyceride, an efficient and uniform production method is a method comprising a step of using a coater device for coating and drying. In such step, drying is preferably hot-air drying. Drying air is at a temperature of preferably 20° C. to 60° C. and particularly preferably 25° C. to 40° C. Preferably, a dew point is 0° C. to 1° C. Preferably, an air flow is 0.5 to 10 m/second. A required time period for drying is a time period during which a solvent is substantially dried. Meanwhile, drying for a long period of time may result in denaturing of a conjugated enzyme, and thus the time period for drying is preferably 1 to 60 minutes. It is also possible to set preferable drying conditions by controlling the temperature, dew point, air speed, and direction of drying air and a time period for drying in each of a plurality of drying zones.

Calcium chloride ($CaCl_2$) may be added to any coating solution. However, it may react with deoxycholic acid and form an aggregate in some cases. As $CaCl_2$ can be dissolved in ethanol, it is preferred that $CaCl_2$ is dissolved in a substrate ethanol solution and is then added.

A reaction reagent that is not dissolved in an organic solvent is separately added by applying it as a water-soluble solution. In order to improve coating suitability and blood development properties, it is preferable to add a binder and a surfactant. A pH buffer, colipase serving as a lipase reaction promoter, and deoxycholic acid may be added to such solution. As above, a reagent is added to a development layer via coating and drying.

Basically, each reaction reagent may be added to any layer upon production, provided that reagent conditions appropriate for reaction can be achieved upon reaction of lipase in a specimen via dissolution and dispersion.

Regarding a method for adding a reagent, dipping or spraying may be carried out as long as a uniform amount of a reagent can be determined. Regarding the order of preparation of individual layers, a method whereby a uniform layer in which a reagent is not degraded is obtained may be used. In some cases, it is also possible to prepare a layer according to the above production method with the use of a porous membrane such as glass fiber filter paper or filter paper and without the use of a support. Also in such case, it is preferable to dry a solution obtained by dissolving a substrate in an organic solvent via hot-air drying.

In view of production, packaging, transportation, storage, measurement operations, and other points, it is preferable to use the integrated multilayer analytical element of the present invention in a manner such that it is cut into square pieces having sides each approximately 10 mm to 30 mm in length or circular pieces having sizes similar to the sizes of the square pieces, following which the pieces are accommodated in slide frames or the like disclosed in the following documents so as to be used as analytical slides: JP Patent Publication (Kokai) No. 57-63452 A (1982); JP Patent Publication (Kokai) No. 54-156079 A (1979); JP Utility Model Publication (Kokai) No. 56-142454 U (1981); JP Utility Model Publication (Kokai) No. 58-32350 U (1983); and JP Patent Publication (Kokai) No. 58-501144A (1983).

The integrated multilayer analytical element of the present invention is used as follows. An aqueous liquid sample in an amount of approximately 5 µl to 30 µl, and preferably approximately 8 µl to 15 µl, is supplied by spotting to a porous development layer according to the methods according to the above documents. If necessary, incubation is carried out at a substantially constant temperature in the range of approximately 20° C. to 45° C. Then, reflective photometry is carried out from the light-permeable support side of the integrated multilayer analytical element in order to observe detectable changes therein, including color change and coloring. Thereafter, the components to be measured in a liquid sample are analyzed based on the principles of colorimetric methods.

The present invention is hereafter described in greater detail with reference to the following examples, although the technical scope of the present invention is not limited thereto.

EXAMPLES

Example 1

Preparation of a Dry Analytical Element Comprising Linear Sodium Dodecylbenzenesulfonate (1) Addition of a Glycerine Coloring Reagent:

A reagent of the following composition was coated as an aqueous solution to a gelatin-undercoated polyethylene terephthalate film having a thickness of 180 µm which was smooth, colorless, and transparent, followed by drying. Subsequently, water was uniformly supplied to the film such that the film became wet. Tricot knitted fabric prepared by knitting (36 gauge) with polyethylene terephthalate spun yarn (corresponding to 50 deniers) was laminated thereon by light pressurization. The gelatin was solidified at a drying temperature of 20° C., followed by drying at 45° C. In addition, the coating solution comprising a pH buffer (PIPES) used was adjusted to have a pH of 6 with a 1 N—NaOH aqueous solution.

Gelatin: 12 g/m$^2$
PIPES (Dojindo Laboratories): 22 g/m$^2$
Magnesium chloride (Wako Pure Chemical Industries, Ltd.): 0.52 g/m$^2$
ATP-2 sodium salt (Oriental Yeast Co., Ltd.): 1.4 g/m$^2$
Polyoxyethylene tridecylether HLB14.8 (Dai-ichi Kogyo Seiyaku Co., Ltd.): 0.55 g/m$^2$
Polyethylene alkyl branched decylether HLB15.9 (Dai-ichi Kogyo Seiyaku Co., Ltd.): 0.059 g/m$^2$
Leuco dye: 0.21 g/m$^2$
Horseradish peroxidase (TOYOBO Co., Ltd): 14 KU/m$^2$
Glycerol kinase (Asahi Kasei Corporation): 3.8 KU/m$^2$
L-α-glycerophosphate oxidase (Asahi Kasei Corporation): 19 KU/m$^2$
1,2-bis(vinylsulfonylacetamide) ethane: 3.3 g/m$^2$ (2) Addition of a Substrate:

A reagent of the following composition was dissolved in ethanol and coated to the above fabric, followed by hot-air drying at a drying temperature of 32° C. with the use of air at a dew point of 0° C.

Calcium chloride (Wako Pure Chemical Industries, Ltd.): 0.18 g/m$^2$
Polyvinylpyrrolidone K90 (BASF): 2.0 g/m$^2$
Triolein (98%, ICN-Biochemical): 1.1 g/m$^2$ (3) Addition of a Lipase Reaction Adjuvant Further, the following reagent was dissolved in water and coated to the above resultant, followed by drying. Thus, a dry analytical element for pancreatic lipase was prepared. In addition, the coating solution comprising a pH buffer (HEPES) was adjusted to have a pH of 8.0 with the use of a 1 N—NaOH aqueous solution.

HEPES (Dojindo Laboratories): 6.1 g/m$^2$
Linear sodium dodecylbenzenesulfonate (Wako Pure Chemical Industries, Ltd.): 0.67 g/m$^2$
Sodium deoxycholate (Wako Pure Chemical Industries, Ltd.): 4.6 g/m$^2$
Sodium taurodeoxycholate: 1.5 g/m$^2$
Metolose: 2.1 g/m$^2$
Monoglyceride lipase (Asahi Kasei Corporation): 4300 U/m$^2$
Pig colipase (Roche) 0.051 g/m$^2$
Ascorbate oxidase (TOYOBO Co., Ltd): 8500 U/m$^2$

Comparative Example 1

A dry analytical element for pancreatic lipase analysis was produced by the same method as that described in Example 1 with the exception that linear sodium dodecylbenzenesulfonate was not contained.

Measurement 1:

Forty-six canine plasma analytes were used. 10 µl each of the analyte was added to the dry analytical elements for pancreatic lipase analysis which were produced in Example 1 and Comparative Example 1, and the dry analytical elements were then heated at 37° C., so that a change in the reflection density at 650 nm was examined for 5 minutes. A commercially available Fuji Dry Chem 7000 was used. With regard to conversion of reflection density to lipase activity, as generally conducted with a Fuji dry chem system, the reflection density was converted to a substrate reacting amount (glycerine level), and correction of faded color was then carried out. Thereafter, lipase activity per analyte per minute was calculated. For a definitive method, Hitachi 7180 was used as an analyzer, and a lipase analysis kit of Roche that was based on the RGGR method was used as a reagent.

Figure 2:
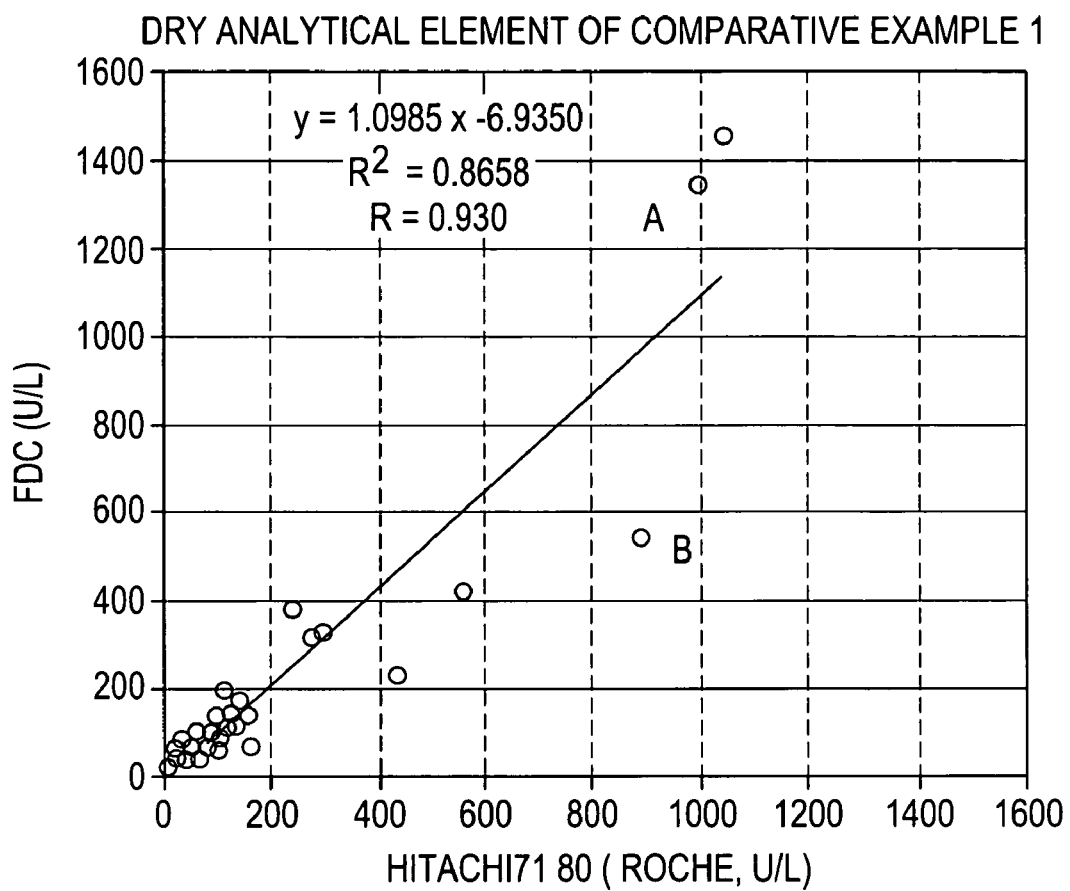
FIG. 2 shows the results of an analysis using the dry analytical element of Comparative example 1.

Multianalyte correlation data are shown in FIGS. 1 and 2. The correlation coefficient was improved to R=0.980 in Example 1, whereas the correlation coefficient was R=0.930 in Comparative Example 1. The analysis of Example 3 was carried out using analytes A and B as shown in FIGS. 1 and 2.

Example 2

Influence of Amounts of Sodium Dodecylbenzenesulfonate and Colipase

Analysis elements were produced by the same production method as that described in Example 1 with the exception that the amounts of sodium dodecylbenzenesulfonate and colipase were changed. A multianalyte correlation was examined using forty-six canine analytes. The results are shown in Table 1. When a lipase analysis slide, to which sodium dodecylbenzenesulfonate had been added, was compared with a lipase analysis slide, to which such sodium dodecylbenzenesulfonate had not been added, it was reconfirmed that a favorable correlation coefficient was obtained when such reagents were used within the amount range as shown in Table 1.

TABLE 1

| Slide No. | Sodium dodecyl-benzenesulfonate ($g/m^2$) | Pig colipase ($g/m^2$) | Correlation coefficient (R) |
|---|---|---|---|
| 2-1 (same as in Example 1) | 0.67 | 0.05 | 0.9801 |
| 2-2 | 0.67 | 0.1 | 0.9744 |
| 2-3 | 0.67 | 0.18 | 0.9819 |
| 2-4 | 1.0 | 0.05 | 0.9785 |
| 2-5 | 1.0 | 0.1 | 0.9760 |
| 2-6 | 1.0 | 0.18 | 0.9765 |
| 2-7 | 1.34 | 0.05 | 0.9754 |
| 2-8 | 1.34 | 0.1 | 0.9752 |
| 2-9 | 1.34 | 0.18 | 0.9786 |
| 2-10 (same as in Comparative example 1) | 0 | 0.05 | 0.9305 |

Example 3

Measurement of Pancreatic Lipase Reaction Time Course by Addition of Sodium Dodecylbenzenesulfonate Dry analytical elements for measurement of pancreatic lipase were produced by the same production method as those described in Examples 1 and 2 with the exception that the amount of sodium dodecylbenzenesulfonate (abbreviated as SDBS in FIGS. 3 and 4) added was changed. "3-1" in Table 2 indicates Comparative example 2.

TABLE 2

| Slide No. | Sodium dodecyl-benzenesulfonate ($g/m^2$) | Pig colipase ($g/m^2$) |
|---|---|---|
| 3-1 (Comparative example 2) | 0 | 0.1 |
| 3-2 | 0.34 | 0.1 |
| 3-3 | 0.67 | 0.1 |

Measurement:

Two analytes (A and B), to which a positive error and a negative error had been imparted, were selected from the multianalyte correlation of Comparative example 1. Measurement was carried out using the pancreatic lipase dry analytical element produced in Example 3, and a comparison was then made on their reaction time courses. As the analytes A and B, the same analytes as those described in the aforementioned multianalyte correlation data of Example 1 and Comparative example 1 were used.

Figure 3:
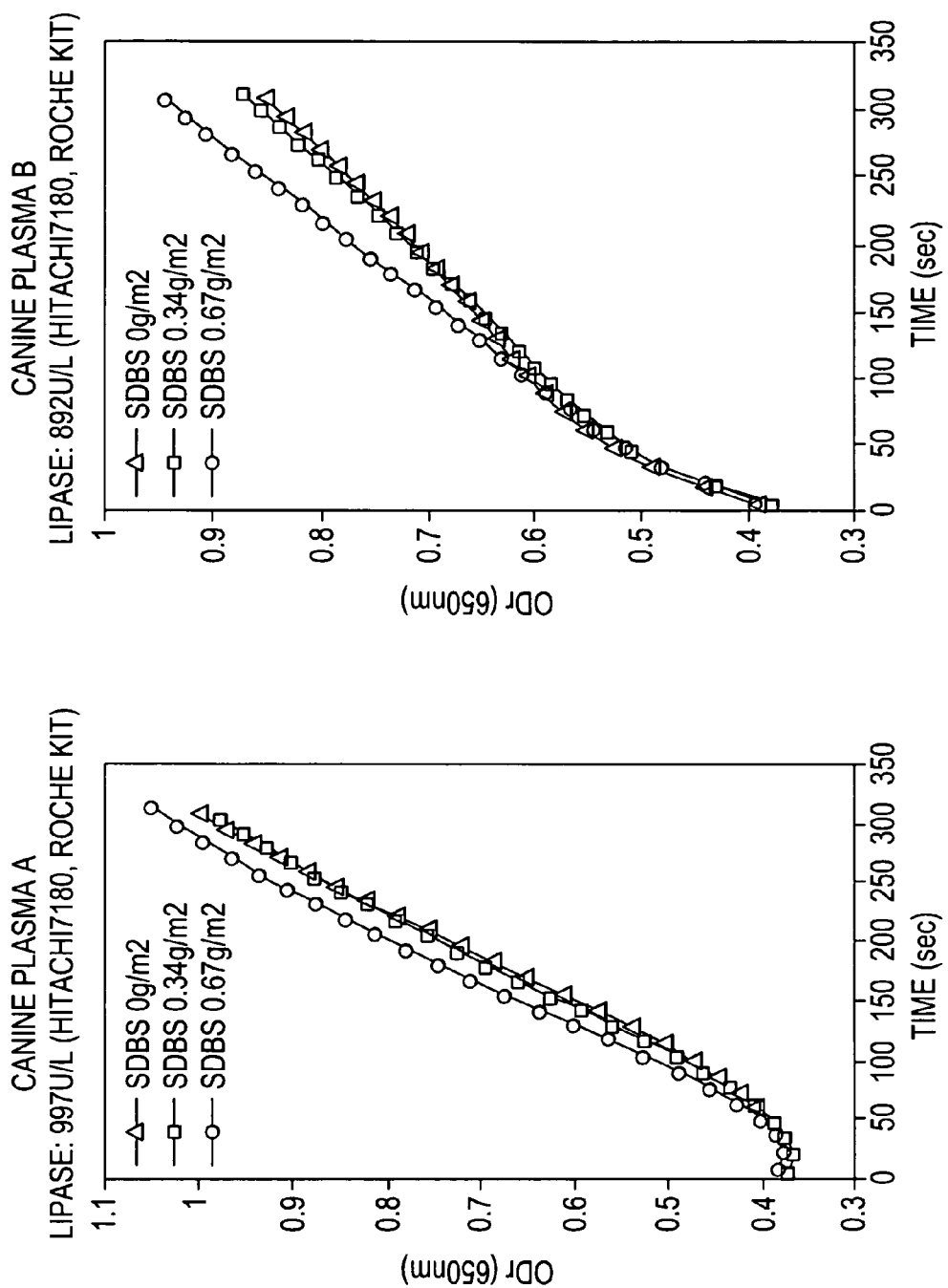
FIG. 3A shows results obtained by measuring analyte A, to which a positive error and a negative error were given in a multianalyte correlation, using the pancreatic lipase dry analytical element produced in Example 3, and then comparing their reaction time courses.
FIG. 3B shows results obtained by measuring analyte B, to which a positive error and a negative error were given in a multianalyte correlation, using the pancreatic lipase dry analytical element produced in Example 3, and then comparing their reaction time courses.

Results:

The results are shown in FIG. 3 (the left figure indicates analyte A, and the right figure indicates analyte B). It was revealed that the lipase reactivity of analyte B, to which a negative error had been given in the multianalyte correlation of Comparative Example 1, was improved by addition of sodium dodecylbenzenesulfonate. On the other hand, in the case of analyte A, to which a positive error had been given, even if such sodium dodecylbenzenesulfonate was added, reactivity was changed only to a small extent. From these results, it could be confirmed that addition of sodium dodecylbenzenesulfonate improved the activity of only the analyte having poor reactivity, so that a multianalyte correlation could be improved.

The invention claimed is:

1. A dry analytical element for measurement of pancreatic lipase contained in a body fluid, which comprises at least one development layer and/or reagent layer containing diglyceride or triglyceride of long-chain alkyl fatty acid having 12 to 22 carbon atoms, monoglyceride lipase, and a glycerine measurement reagent, wherein the development layer and/or the reagent layer comprise two or more types of anionic surfactants and at least one type of the anionic surfactant is alkylarylsulfonate.

2. The dry analytical element according to claim 1, wherein the alkylarylsulfonate is alkylbenzenesulfonate.

3. The dry analytical element according to claim 2, wherein the alkylbenzenesulfonate is alkylbenzenesulfonate, the chain length of an alkyl group of which consists of 10 to 14 carbon atoms.

4. The dry analytical element according to claim 3, wherein the alkylbenzenesulfonate is a linear dodecylbenzenesulfonic acid sodium salt.

5. The dry analytical element according to claim 1, wherein the amount of alkylarylsulfonate added is 0.1 to 10 $g/m^2$.

6. The dry analytical element according to claim 1, wherein the triglyceride is triolein.

7. The dry analytical element according to claim 1, wherein the monoglyceride lipase is *Bacillus stearothermophilus* H-165-derived monoglyceride lipase.

8. The dry analytical element according to claim 1, wherein the glycerine measurement reagent is composed of glycerol kinase, glycerophosphate oxidase, and a coloring reagent.

9. The dry analytical element according to claim 1, wherein the dry analytical element is composed of a water-impermeable support, a reagent layer, and a development layer.

10. The dry analytical element according to claim 1, wherein the development layer is made of fabric or a porous membrane.

11. The dry analytical element according to claim 1, wherein the porous membrane is a porous membrane formed with polyvinylsulfone or acetylcellulose or a porous membrane formed with microbeads.

12. The dry analytical element according to claim 1, wherein the amount of monoglyceride lipase added is 8000 $U/m^2$ to 1000 $U/m^2$.

13. The dry analytical element according to claim 1, which is produced by a method comprising a step of adding diglyceride or triglyceride dissolved in lower alcohol or acetone to a development layer or a reagent layer and then drying it.

14. The dry analytical element according to claim 13, wherein the method of drying diglyceride or triglyceride is hot-air drying.

15. The dry analytical element according to claim 13, wherein diglyceride or triglyceride is dissolved in methanol, ethanol, propyl alcohol, or acetone.

16. A method for measuring pancreatic lipase contained in a body fluid, which comprises applying a body fluid to the dry analytical element of claim 1.

17. The method for measuring pancreatic lipase contained in a body fluid according to claim 16, wherein the body fluid is canine blood.

* * * * *